US005720805A

United States Patent [19]

Wellinghoff et al.

[11] Patent Number: 5,720,805

[45] Date of Patent: Feb. 24, 1998

[54] TITANIUM-TIN-OXIDE NANOPARTICLES, COMPOSITIONS UTILIZING THE SAME, AND THE METHOD OF FORMING THE SAME

[75] Inventors: Stephen T. Wellinghoff, San Antonio, Tex.; Domnica Cernasov, Ringwood, N.J.

[73] Assignee: Southwest Research Institute, San Antonio, Tex.

[21] Appl. No.: 714,933

[22] Filed: Sep. 27, 1996

Related U.S. Application Data

[60] Continuation-in-part of Ser. No. 298,836, Aug. 31, 1994, Pat. No. 5,670,583, which is a division of Ser. No. 47,750, Apr. 13, 1993, Pat. No. 5,372,796.

[51] Int. Cl.⁶ .................... C04B 35/453; C04B 35/457; C04B 35/46
[52] U.S. Cl. ................. 106/441; 501/12; 501/134; 501/905; 423/598; 423/610; 423/618; 424/650; 424/600
[58] Field of Search ............... 106/441; 501/12, 501/134, 905; 502/350; 423/598, 610, 618; 424/59, 650, 600

[56] References Cited

U.S. PATENT DOCUMENTS

| | | | |
|---|---|---|---|
| 4,448,898 | 5/1984 | Sun | 502/350 |
| 4,849,140 | 7/1989 | Wellinghoff et al. | |
| 5,160,455 | 11/1992 | Clark et al. | |
| 5,215,580 | 6/1993 | Elfenthal et al. | 106/441 |
| 5,231,156 | 7/1993 | Lin | |
| 5,316,855 | 5/1994 | Wang et al. | |
| 5,337,129 | 8/1994 | Badesha | |
| 5,372,796 | 12/1994 | Wellinghoff | |

*Primary Examiner*—Michael Marcheschi
*Attorney, Agent, or Firm*—John L. Sigalos

[57] ABSTRACT

There are disclosed stabilized Ti-Sn-O nanoclusters formed by complexing Ti-Sn-O nanoclusters with a salt of an alpha-hydroxy acid and also complexed nanoclusters with increased charge transfer interaction formed by annealing the complexed nanoclusters. Also disclosed are compositions for protection against ultraviolet radiation in which the nanoclusters are utilized with the usual topical carriers in an amount to give the level of sun protection factor (SPF) desired. Further disclosed is the method of making the nanoclusters involving acid hydrolyzing a titanium alkoxide and then reacting the hydrolyzed alkoxide with a tin halide.

13 Claims, 4 Drawing Sheets

|  | TEST 1 |  | TEST 2 |  |
|---|---|---|---|---|
| SUNSCREEN PROTECTION FACTOR: | 2.2 | 0.1 | 2.5 | 0.4 |
| MEAN ABSORBANCE RATIO: | 0.16 | 0.02 | 0.27 | 0.02 |

| WAVELENGTH | ABS | MPF |
|---|---|---|
| 290 | 0.65 | 4.45 |
| 295 | 0.59 | 3.85 |
| 300 | 0.54 | 3.45 |
| 305 | 0.47 | 2.95 |
| 310 | 0.40 | 2.5 |
| 315 | 0.33 | 2.15 |
| 320 | 0.27 | 1.85 |
| 325 | 0.22 | 1.65 |
| 330 | 0.19 | 1.55 |
| 335 | 0.15 | 1.4 |
| 340 | 0.13 | 1.35 |
| 345 | 0.11 | 1.3 |
| 350 | 0.11 | 1.3 |
| 355 | 0.08 | 1.2 |
| 360 | 0.08 | 1.2 |
| 365 | 0.08 | 1.2 |
| 370 | 0.06 | 1.15 |
| 375 | 0.06 | 1.15 |
| 380 | 0.06 | 1.15 |
| 385 | 0.06 | 1.15 |
| 390 | 0.06 | 1.15 |
| 395 | 0.04 | 1.1 |
| 400 | 0.04 | 1.1 |

| | TEST 1 | | TEST 2 | |
|---|---|---|---|---|
| SUNSCREEN PROTECTION FACTOR: | 1.5 | 0 | 1.7 | 0.2 |
| MEAN ABSORBANCE RATIO: | 0.14 | 0.03 | 0.21 | 0.03 |

| WAVELENGTH | ABS | MPF |
|---|---|---|
| 290 | 0.39 | 2.45 |
| 295 | 0.34 | 2.0 |
| 300 | 0.32 | 2.1 |
| 305 | 0.28 | 1.9 |
| 310 | 0.23 | 1.7 |
| 315 | 0.18 | 1.5 |
| 320 | 0.15 | 1.4 |
| 325 | 0.11 | 1.3 |
| 330 | 0.10 | 1.25 |
| 335 | 0.06 | 1.15 |
| 340 | 0.06 | 1.15 |
| 345 | 0.06 | 1.15 |
| 350 | 0.04 | 1.1 |
| 355 | 0.04 | 1.1 |
| 360 | 0.02 | 1.05 |
| 365 | 0.02 | 1.05 |
| 370 | 0.02 | 1.05 |
| 375 | 0.02 | 1.05 |
| 380 | 0.02 | 1.05 |
| 385 | 0.02 | 1.05 |
| 390 | 0.02 | 1.05 |
| 395 | 0.02 | 1.05 |
| 400 | 0.02 | 1.05 |

TITANIUM-TIN-OXIDE NANOPARTICLES, COMPOSITIONS UTILIZING THE SAME, AND THE METHOD OF FORMING THE SAME

CROSS-REFERENCE TO RELATED APPLICATIONS

The instant application is a Continuation-in-Part of U.S. application Ser. No. 08/298,836, filed Aug. 31, 1994, now U.S. Pat. No. 5,670,583 which is a Division of U.S. application Ser. No. 08/047,750, filed Apr. 13, 1993, now U.S. Pat. No. 5,372,796. The entirety of the specification and claims of the foregoing applications are specifically incorporated herein by reference.

BACKGROUND OF THE INVENTION

The present invention relates to novel Ti-Sn-O nanoparticles compositions for protection against ultraviolet radiation comprising the same, and method of forming such nanoparticles.

U.S. Pat. No. 5,372,796 describes a method of making metal oxide clusters and in the compilation of selected invited papers for the International Symposium on Advances in Sol-Gel Processing and Applications, August 1993, there is disclosure of a process by which nanosized oxide particles can be grown in a non-aqueous medium and which are coated with trialkyl siloxane groups which serve to terminate growth and assure that the particles can be redispersed to make clear solutions in many solvents. Clear solutions of the particles in polymerizable solvents using up to 40% by volume of the uncoagulated, nanosized particles can also be made and polymerization of the mixture yields transparent plaques and films.

It is believed that titanium oxide nanoclusters have a surface that is highly acidic consisting of several different types of Lewis acid sites. Such condition is known to exist on titanium oxide. The coordinative potential of hydroxylated titanium ions is also well known and strong complexes are formed with alpha-hydroxy carboxylic acids which can be neutralized with amines and metal hydroxides. In some cases electron transfer complexes with electron donors can also be formed where the $Ti^{+4}$ ions can be completely reduced to $Ti^{+3}$ ions.

Generally, however, titanium oxide particles, while they can be made initially in very small particle sizes, about 50Å, they can seldom be supplied as such due to the fact that the particles are always highly coagulated. Also, while titanium oxide nanoclusters appear to be indefinitely stable at room temperature in highly acidic solutions, heating or dilution of such particles results either in a flocculant precipitate or an elastic gel.

Much work has also been done with titanium oxide-based sols and gels, in which the size of the nanoclusters is presumably much smaller than the wavelength of visible light.

These characteristics of titanium oxide have been utilized in certain types of ultraviolet radiation absorbing compositions, such as sunscreen compositions, where titanium dioxide has long been in use. It is a decided advantage in that titanium dioxide has been approved for use in cosmetics and it is known that amorphous titanium oxide or oxyhydride will absorb short wavelengths. Thus, for particle sizes of titanium oxide approaching the wavelength of visible light, the high extinction coefficients of the titanium oxide translate into a very high reflectivity for radiation that would normally be absorped by nanosized particles. However, titanium oxide nanoclusters which have superior UV absorbing properties are not satisfactorily used in sunscreen compositions because of their noted lack of stability.

At the present time for UV absorbing compositions and especially for sunscreens, it is also known to utilize organic chromophores for long term UV photostabilization of polymers. These include salicylates, benzophenones, cinnamates, benzotriazoles, and the like. The important molecular characteristic of all of the strong UV absorbers is the proximity of an hydroxy group to an atom X with an unpaired electron, which can form a planar X—H—O bond in the excited state. Thus, certain benzophenones, cinnamates, and salicylates are acceptable for sunscreens or other uses in cosmetics for use in the 200–340 nm range. Unfortunately, with respect to these organic compounds, particularly the cinnamates, they are irritating to the skin, especially at the high concentrations necessary to generate high sun protective factors (SPF), normally an SPF above 15. This problem is especially acute for individuals and animals with highly sensitive skin or subject to skin displasias or melanomas.

It has therefore been desired to utilize non-organic sunscreen components to avoid these sensitivity problems. This problem with sensitivity is also present with a newly approved sunscreen butyl-methoxydibenzoylmethane which provides good absorbants both in the UVA and UVB ranges.

In these sunscreens the organic chromophores, as is conventional, are mixed with lipid based emollients or occlusive agents, and emulsifiers to make an oil in water emulsion which scatters light. This typically works in the following manner. When the cream is applied to the skin as a thin coating, the water rapidly evaporates and the coating becomes predominantly single phase with a much lower light scattering. The solar blocking power (absorption and backscattering) of any of these mixtures on the skin is a function of the skin surface roughness, the solubility of the cosmetics base formulation in the skin with the assistance of the emulsifier, and the refractive index differences between the swollen skin layer and the overlying insoluble phase.

SUMMARY OF THE INVENTION

The present invention provides novel stabilized titanium tin oxide nanoparticles, methods of forming the same, and compositions for protection against ultraviolet radiation utilizing the same which eliminate problems of skin sensitivity and which can be applied as vanishing compositions with a pleasing cosmetic appearance and which have a very effective absorption of light between 200–340 nm.

Briefly, the present invention comprises a nanocluster stabilized against coagulation at pH>1 in aqueous solution and as a dry powder at temperatures up to about 290° C. consisting of a Ti-Sn-O nanocluster complexed with a salt of an alpha-hydroxy acid.

The invention also comprises a composition for protection against ultraviolet radiation comprising a carrier and Ti-Sn-O charge transfer complex nanocluster.

Further, the invention comprises a method of making a Ti-Sn-O charge transfer complex nanocluster comprising hydrolyzing a titanium oxide in an aqueous solution with an acid and then reacting the hydrolyzed titanium oxide with $SnX_2$ in which X is a halide.

DETAILED DESCRIPTION

Figure 1:
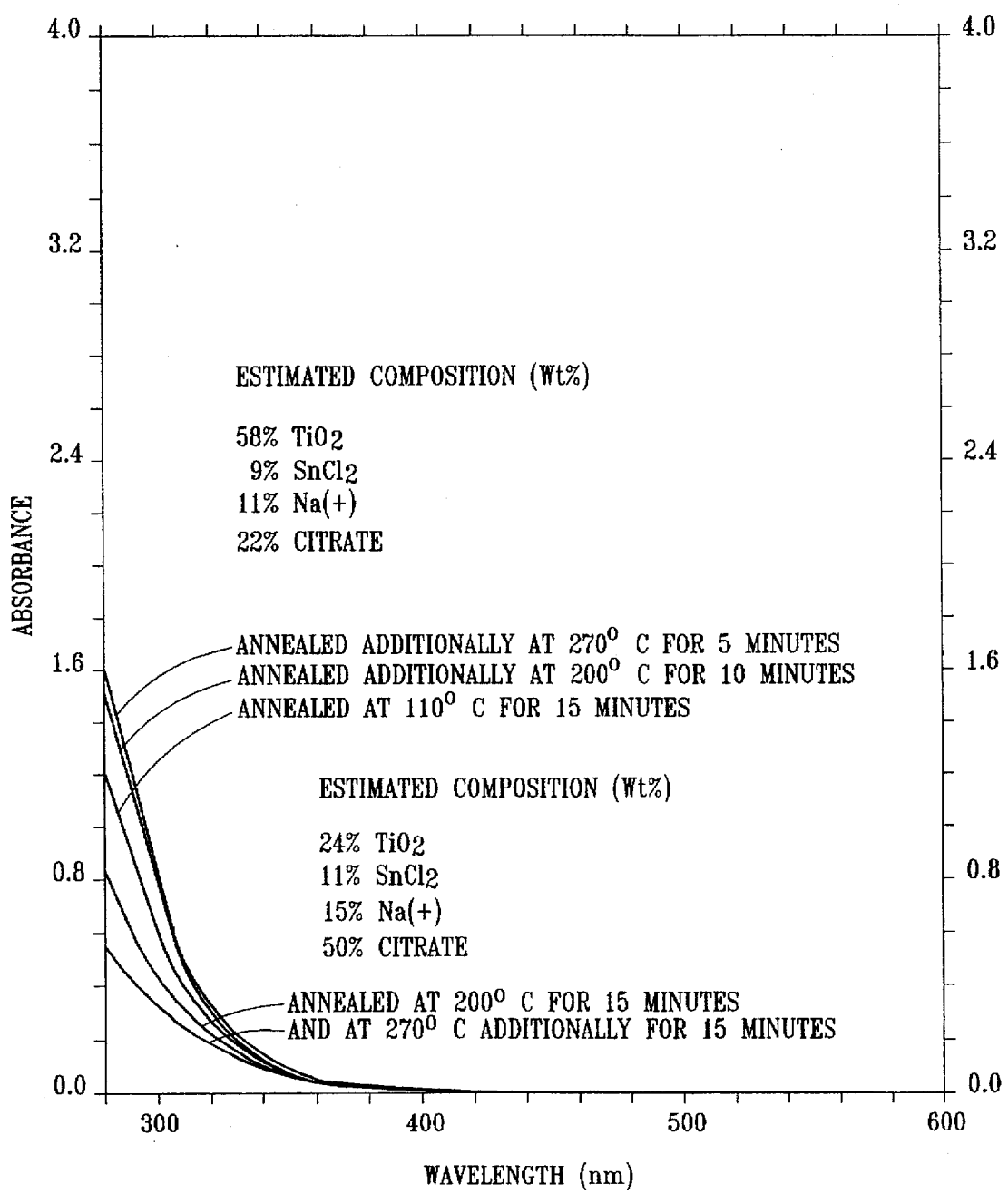
FIG. 1 is a graph showing the UV-visible spectra of the two powders of Example 1 hereof, at wavelengths of 280 to 600 nm.

With respect to the method of the present invention, stabilized titanium-tin-oxide nanoclusters i.e., nanometer sized clusters, are formed for the purpose of enhanced absorption of the UV radiation. It is particularly desired to form alpha-hydroxy acid complexes of the Ti-Sn-O nanoclusters to form one phase solution at volume fractions up to 40% in aqueous as well as alcoholic solutions. This is quite useful in minimizing cosmetically displeasing light scattering when applied to the skin as part of a topical preparation.

The method comprises first reacting a titania nanocluster solution under acidic conditions with a tin halide, preferably a chloride, although bromide and iodide salts can also be used. Any strong inorganic or organic acid can be used to acidify with HCl preferred, but suitable other acids are HBr, HF, $H_2SO_4$, $CF_3(OOH)$, and the like. The $SnCl_2$ is preferably in solution in alcohol or a concentrated acidic solution, preferably at a concentration of about 0.1 to 1M. The molar ratios of the reactants is approximately 0.1 to 0.3 Sn to 1 Ti. These reactions are carried out under ambient conditions for a time sufficient to produce titania nanoclusters complexes with Sn. Dependent upon the particulars of the reactants, this can vary from about 5° to 40° C. for 1 minute to 1 hour with the optimum reaction time and temperature for any given set of reactants being determined by routine experimentation.

These complexes as such are not stable and must be stabilized against solution coagulation in accord with the present invention by further reacting the resultant Ti-Sn-O nanoclusters with a titanium alkoxide, preferably of the formula $Ti(OR)_4$ in which R is a C3 to C4 alkyl group, preferably an isopropyl group at room temperature (0°–40° C.) for 1 minute to 1 day in methanol-water solutions. The ratio of Ti-Sn-O nanocluster to the $Ti(OR)_4$ is preferably 1 to 0.25 to 0.5. After this reaction, the resultant reactant is complexed with a salt of an alpha-hydroxy acid such as citric, malic, lactic, gycolic and tartaric acid. Also suitable are the alpha-hydroxy acid terminated oligomers of polyvinyl alcohol or polyvinyl pyrrolidone. A particularly suitable salt is trisodium citrate and there is utilized for each mol of Ti-Sn-O nanoclusters 0.25 to 3 mols of the trisodium citrate in water. It is also possible to adjust the pH as by the addition of an alkali such as sodium hydroxide without precipitation of the nanoclusters. This can be accomplished in water-methanol solutions at room temperature (0°–40° C.)

The solution can be maintained as such or a powder formed by removal of the water, as by vacuum evaporation. The result is a yellow powder. This stabilized powder can be redissolved in water or alcohols even after heating up to 290° C. for long as one-half hour.

While various solvents can be utilized to dissolve the resultant powder, any conventional cosmetic solvent, such as glycerol and water is suitable for the purpose and these have been found to be especially effective solvents capable of dissolving up to 40 wt. % of the citrate complex of the Ti-Sn-O nanoclusters.

It is desired also to anneal the resultant powder to improve its properties. More particularly, annealing increases the density of the powder by improving the Ti-O-Sn charge transfer interaction and removing volatiles. Annealing is preferably carried out in air at 200°–280° C. for 5 minutes to 1 hour. An especially beneficial aspect of the annealed Ti-Sn-O citrate complex is that the extinction coefficient of such complex between 280–340 nm is at least three times higher, based on the total concentration of Ti-Sn-O than is a Ti-O citrate complex. This much higher extinction coefficient per gram of complex for the Ti-Sn-O material is of a special advantage in minimizing the application thickness of the composition containing the same required for high SPF in the UVA and UVB.

These stabilized Ti-Sn-O complex nanoclusters will not coagulate at a pH>1 in aqueous solution and as a dry powder at temperatures up to about 290° C. They have a particle size of about 20 Å to 100 Å for optimum UV absorption. While not presently entirely understood, it is believed that an increase in pH during reaction at higher temperature will increase size.

Thus, the resultant complexes are highly novel and, as noted, are especially for use in compositions as UV absorbers.

While the novel stabilized nanoclusters of the instant invention can be utilized in a wide variety of compositions where ultraviolet radiation protection is required, as in furniture polishes, sunscreens, paints, enamels, plastic articles, and the other known articles in which UV absorbers are utilized, they will be more specifically described in connection with sunscreen compositions for topical application. It is a particularly useful characteristic of the Ti-Sn-O citric complexes of the present invention that either as a dry powder or as 40% glycerol or aqueous solutions, they can be emulsified with the usual emollients, surfactants, moisturizers/humectants, pH adjusters, thickness/film formers, sunscreen filters, fragrances, colorants, chelating agents, preservatives, and the like, presently conventionally used to make alcohol or water based sunscreen compositions of various SPF. Specific examples of these additives are listed below.

Emollients:

Cetyl esters, cetyl lactate, cetyl palmitate, corn oil, diisopropyl adipate, diisopropyl dimer dilinolate, grape seed oil, hydrogenated castor oil, hydrogenated coconut oil, hydrogenated soybean oil, isopropyl palmitate, isopropyl myristate, lauryl lactate, maleated soybean oil, octyl dodecanol, octyl isononanoate ether, sodium hyaluronate, soluble collagen, squalene, sterol esters, and the like.

Surfactants:

Cetoaryl alcohol, cetyl alcohol, DEA-cetyl phosphate, disodium laureth sulfosuccinate, glycol distearate, Laneth-40, lauryl lactate, magnesium lauryl sulphate, Oleth-3, PEG-2 diisononanoate, PEG-150, PEG-15 cocamine, PEG-40 hydrogenated castor oil, PEG-8 laurate, PEG-20 stearate, Polysorbate 20, PPG-4 myristyl ether acetate, sorbitan laurate, sorbitan stearate, Stearate-10, and the like.

Moisturizing/Humectants:

Glycerine, butylene glycol, propylene glycol, sodium hyaluronate, Aloe vera, glucose, Glycereth-26, Glycereth-7 triacetate, lactic acid, lactose, PEG-6, PEG-32, and the like.

pH Adjusters:

Triethanolamine, sodium hydroxide, ammonium hydroxide, citric acid, disodiium phosphate, glycolic acid, potassium hydroxide, aminomethyl propanol, and the like.

Thickeners/Film formers:

Acrylic/acrylate copolymer, Carbomer 934, Carbomer 941, hydroxypropylcellulose, hydroxypropyl methylcellulose, Xanthan gum, magnesium aluminum silicate, and the like.

Sunscreen Filters:

Octyl methoxycinnamate, octyl dimetyl PABA, benzophenone 1, benzophenone 3, benzophenone 9, Drometrizole, octyl salicylate, phenyl benzimidazole-5 sulphonic acid, and the like.

As will be recognized, it is also often desired to include coloring matter and fragrances in such compositions and these and the other additives noted above can be included in the sunscreen compositions in their usual amounts and for the usual effects.

The invention will be described in connection with the following examples which are set forth for purposes of illustration only.

EXAMPLE 1

Titania based nanoclusters were prepared by admixing 25 ml ($8.4 \times 10^{-2}$ mole) of titanium isopropoxide with 100 ml 1M HCl (0.1 mole HCl; 5.56 mole $H_2O$) to make an initially cloudy solution which cleared within 2 hours. After aging from 2 hours to 1 day attempts were made to rotoevaporate this solution to dryness at 80° C. However, a white coagulate formed that was insoluble even in concentrated HCl. It was also observed that precipitation would occur at room temperature for pH>1.

Since the very active surface hydroxyls on the surface of the titanium oxide nanoclusters are responsible for the fusion of the particles, these groups were neutralized and complexed with the trisodium citrate dihydrate ($Na_3C$).

1.3 grams of titania nanoclusters was dissolved in 2 ml of water and to it dropwise added 1.5 g trisodium citrate dihydrate ($Na_3C$) dissolved in 3 ml water which was sufficient to increase the pH to 4. Adding 3.0 g of $Na_3C$ increased the pH to 7. After drying under vacuum at 80°–90° C., the resultant white powder could be heated to 270° C. without insolubilization, indicating that the surface Ti-OH had been effectively complexed.

The UV-vis spectrum of a water solution of a 1:1 weight ratio of clusters to $Na_3$ citrate that had been annealed at 200° C. in air for several hours shows a continuous increase in extinction coefficient from 360 nm to 200 nm due to loss of solvent. Citrate only makes a small contribution to the absorption around 210–200 nm. The measured extinction coefficient based upon the titanium oxide cluster weight is 300 nm–5600 $cm^{-1}$ and 320 nm–2300 $cm^{-1}$.

EXAMPLE 2

A titania nanocluster charge transfer complex with Sn in water was prepared by admixing 25 ml ($8.4 \times 10^{-2}$ mole) of titanium isopropoxide with 100 ml 1M HCl (0.1 mole HCl; 5.56 mole $H_2O$) to make an initially cloudy solution which cleared within 2 hours. After aging from 2 hours to 1 day, 3.125 g of $SnCl_2$ in 20 ml MeOH ($1.65 \times 10^{-2}$ mole) that had been filtered was added with stirring to the unconcentrated titanium nanocluster solution. The resultant yellow hue was indicative of a Ti-O-Sn surface complex.

Other methods of tin addition were attempted in order to minimize the amount of water added to the mixture which would have to be evaporated later in the process. This included dissolving $3.33 \times 10^{-3}$ moles of $SnCl_2$ in 0.826 ml concentrated HCl ($3.47 \times 10^{-2}$ mole $H_2O$; $9.91 \times 10^{-3}$ mole HCl) and then adding $8.4 \times 10^{-3}$ mole titanium isopropoxide. A very bright orange color appeared which evolved into a lighter orange over several seconds.

After the initial addition of 1 ml of water to this mixture, a yellow precipitate formed. However, the addition of two more ml of water was sufficient to make a clear yellow solution. The visible and UV absorptivity of this solution could be increased by heating a diluted version of this solution up to 70° C., where precipitation occurred.

Since a precipitate appeared in these solutions over a period of several days, the above procedure was repeated except that the additional step of adding an additional $0.7 \times 10^{-2}$ mole of titanium isopropoxide to the mixture was used to seal off the surface chemisorbed Sn that was responsible for phase separation. This treatment resulted in a clear, yellow solution after about 2 minutes that remained clear indefinitely.

Although the solution of these three layer nanoclusters could be pumped to dryness at 50°–60° C. to form a very acidic yellow powder (Ti-Sn-O) that could be redissolved in water, heating to 200° C. for times as short as 10–20 minutes insolubilized the powder.

Again, as with the single component titania nanoclusters, the active surface groups were complexed with $Na_3C$ to neutralize the acidity and thermally stabilize the clusters. The solution was vacuum evaporated at 90° C. to a dry yellow powder that was readily soluble in water and glycerol at weight fractions up to 40%.

It was not necessary to completely neutralize the Ti-Sn-O solution with $Na_3C$. In a typical procedure 0.771 g of Ti-Sn-O was dissolved in water, mixed with 0.385 g $Na_3C$ in water, neutralized to pH=5 with 1N NaOH solution (1.5 ml), and evaporated to dryness under vacuum. The yellow powders prepared in such a fashion could be annealed at 270° C. for 15–30 minutes in air and redissolved in both water and glycerol.

The UV-visible spectra of two powders, each dissolved in a 5% water solution, and containing varying amounts of Ti-Sn-O and $Na_3C$ neutralized with sodium hydroxide to pH=5, was obtained from a 15 micron thickness cast between two quartz plates. There is a substantial shift in the spectrum toward the visible upon complexation of the titania nanoparticles with Sn as is shown in FIG. 1.

As expected the powder with the highest Ti-Sn-O content and highest density, assured by annealing at 270° C. in air, possessed the highest extinction coefficient in the near UV. The extinction coefficients ($cm^1$) for a 1:1 $TiO_2$:$Na_3C$ by weight and the 58 wt % $TiO_2$ in water solutions from FIG. 1 are compared in Table I.

TABLE I

|  | 280 nm | 300 nm | 320 nm |
|---|---|---|---|
| $TiO_2$ | 13,560 | 5600 | 2300 |
| Ti—Sn—O 270° C. (ann) | 31,840 | 17,910 | 6900 |

EXAMPLE 3

Two water in oil cosmetic formulations (A and B) were made with two different loadings of the Ti-Sn-O complexes, 3 wt. % (A) and 5 wt. % (B). The Ti-Sn-O complexes were prepared by diluting 40 parts by weight of the complex with 60 parts by weight glycerin and 60 parts by weight water. The mixture was boiled at 100° C. for approximately 1 hour until all solids (the complex) dissolved and water evaporated. A thick, yellowish, clear solution was obtained. For formulation A (3 wt. % pure Ti-Sn-O) 7.5 wt. % was incorporated with the components listed below and for formulation B (5 wt. % pure Ti-Sn-O) 12.5 wt. %.

The components are set forth in Table II, in which proportions are in % by weight.

TABLE II

|                              | A     | B     |
|------------------------------|-------|-------|
| Cetyl Dimethicone Copolyol   | 2.50  | 2.50  |
| Octyl Palmitate              | 4.00  | 4.00  |
| Octyl Stearate               | 1.50  | 1.50  |
| Cethyl Dimethicone           | 1.00  | 1.00  |
| Hydrogenated Castor Oil      | 0.50  | 0.50  |
| Microcrystalline Wax         | 1.00  | 1.00  |
| Cyclomethicone               | 7.50  | 7.50  |
| Diisopropyl Dimer Dilinoleate| 2.00  | 2.00  |
| Octyldodecyl Neopentanoate   | 9.50  | 7.50  |
| Ti—Sn—O/Glycerin             | 7.50  | 12.50 |
| Water, distilled             | 61.75 | 58.70 |
| NaCl                         | 0.60  | 0.60  |
| Phenoxyethanol               | 0.50  | 0.50  |
| Fragrance (Pritania 33133T)  | 0.15  | 0.20  |

Figure 2:
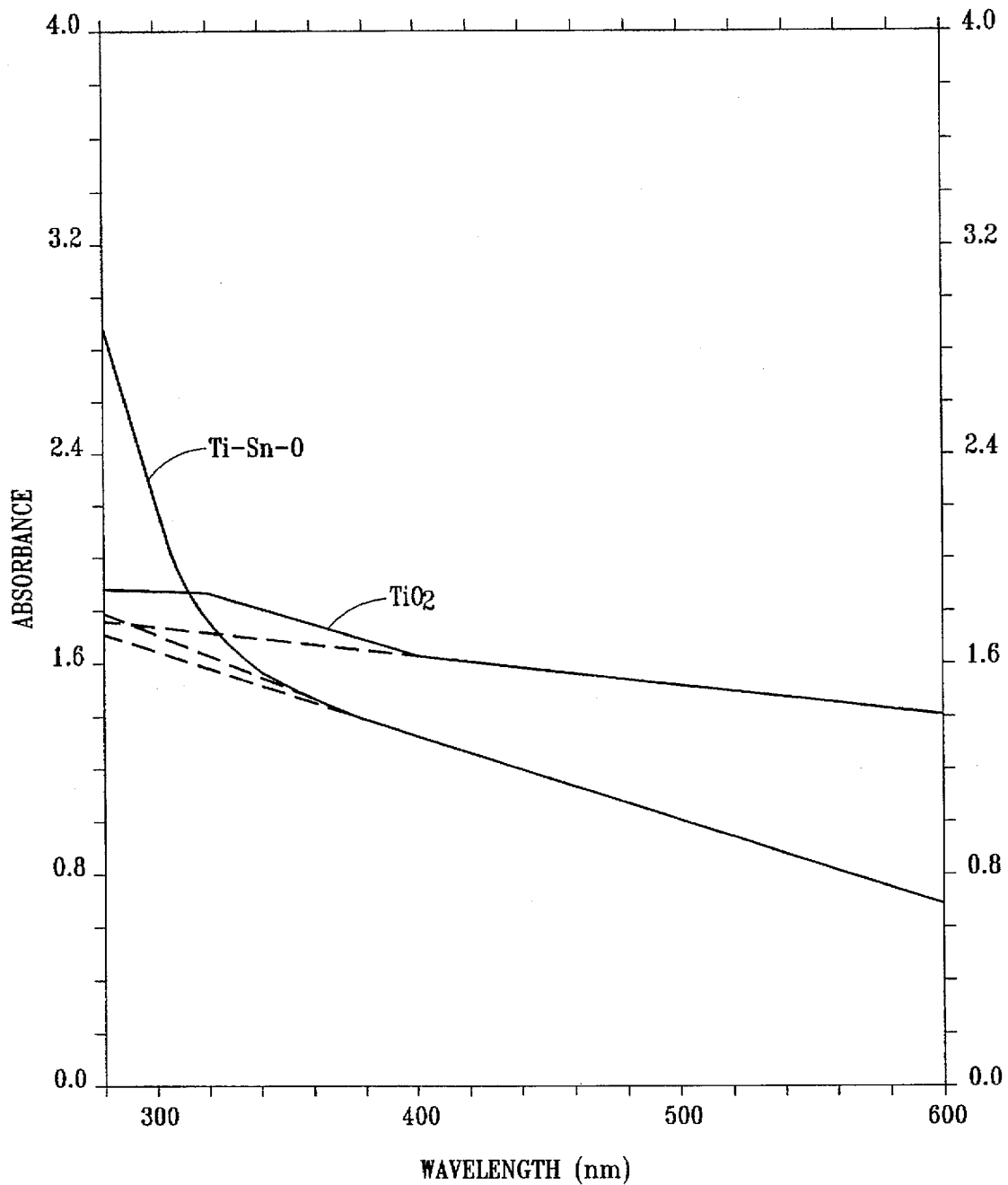
FIG. 2 is a graph showing a comparison of the absorption spectrum of micronized $TiO_2$ and Ti-Sn-O formulations at path length of 15 microns at wavelengths of 280–600 nm.

FIG. 2 is a comparison between a 5% by weight micronized $TiO_2$ formulated into a cosmetics base and a 5% by weight 3:1 Ti-Sn-O:$Na_3C$ (formulation "B" above) that was first dissolved in glycerol at 40 weight % and then dispersed in a cosmetics base. The absorptivity of the Ti-Sn-O mixture is clearly much higher below 320 nm, but the rather frequency independent (non-dispersive) scattering of the micronized $TiO_2$ mixture clearly dominates above 320 nm.

Figure 3:
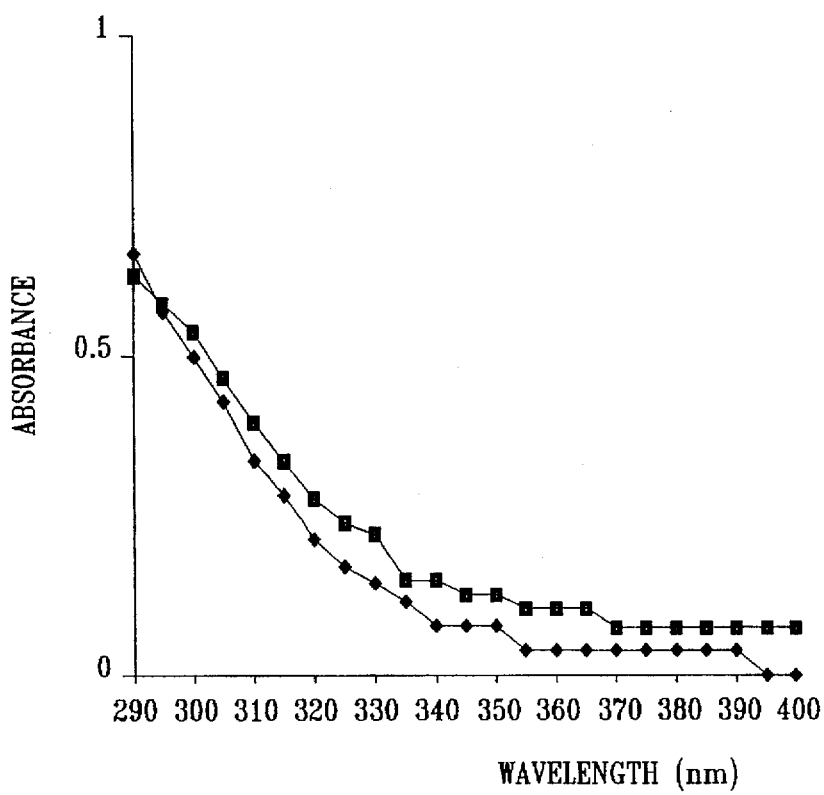
FIGS. 3 and 4 are graphs showing the in vitro sun protective factors of formulations A and B of Example 3 thereof.
Figure 4:
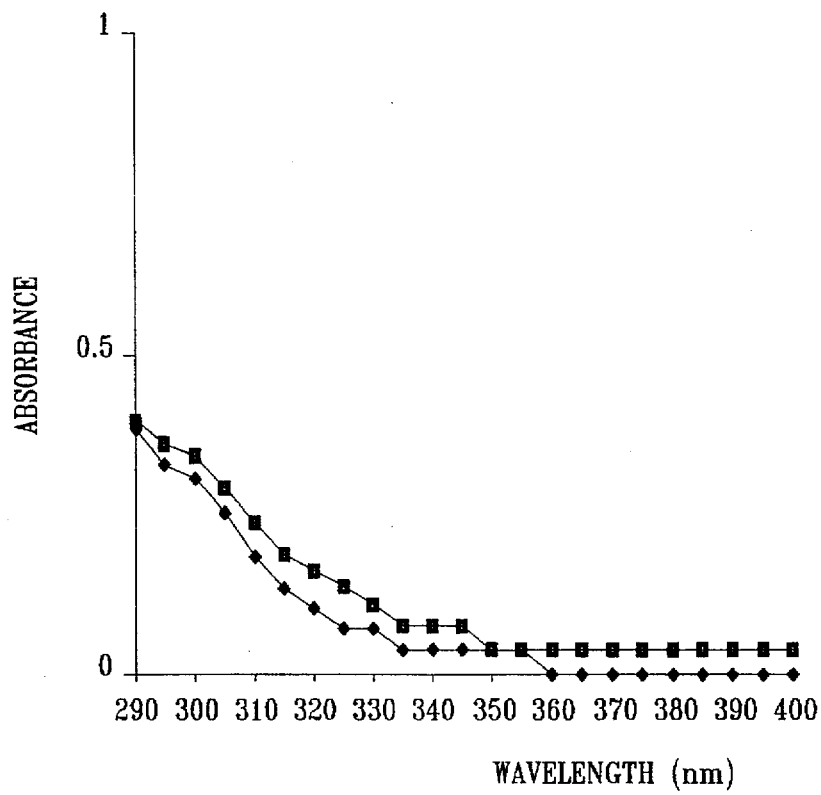

FIGS. 3 and 4 show the in vitro SPF (sun protection factor) calculations for formulations A and B.

It will be evident that in forming compositions for topical application for protection against ultraviolet radiation, the amount of nanoclusters added to the carrier can vary widely dependent upon the degree of protection (SPF) desired. The particular amount of nanoclusters added to give the SPF desired for any given carrier can be determined by routine experimentation with the foregoing examples setting forth SPF calculations for an illustrative carrier with varying amounts of nanoclusters.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A stabilized nanometer size cluster comprising Ti-Sn-O clusters complexed with a salt of an alpha-hydroxy acid.

2. The cluster of claim 1 wherein the complexed cluster is annealed.

3. The cluster of claim 1 or 2 wherein said acid is citric acid.

4. The cluster of claim 1 or 2 wherein said salt is trisodium citrate.

5. A composition for protection against ultraviolet radiation comprising a carrier and stabilized nanometer size Ti-Sn-O charge transfer clusters complexed with a salt of an alpha-hydroxy acid, wherein the complexed clusters are present in an amount effective to absorb ultraviolet radiation.

6. The composition of claim 5 wherein the complex clusters are annealed.

7. The composition of claim 5 or 6 wherein said clusters are present in an amount of at least about 3 wt. % for each 100 wt. % of said composition.

8. The composition of claim 5 or 6 wherein said clusters comprise nanometer size Ti-Sn-O clusters complexed with trisodium citrate.

9. The method of making nanometer size Ti-Sn-O charge transfer complex clusters comprising hydrolyzing a titanium alkoxide in an aqueous solution with an acid and then reacting the hydrolyzed titanium alkoxide with $SnX_2$, in which X is a halide, at a temperature and for a time sufficient to form said clusters.

10. The method of claim 9, further comprising the step of stabilizing said clusters by complexing them with a salt of an alpha-hydroxy acid.

11. The Method of claim 10, further comprising the step of annealing the complexed clusters.

12. The method of claim 10 or 11 wherein said acid is citric acid.

13. The method of claim 10 or 11 wherein said salt is trisodium citrate.

* * * * *